(12) United States Patent
McElhanon et al.

(10) Patent No.: US 7,622,596 B1
(45) Date of Patent: Nov. 24, 2009

(54) THERMALLY CLEAVABLE SURFACTANTS

(75) Inventors: James R. McElhanon, Manteca, CA (US); Blake A. Simmons, San Francisco, CA (US); Thomas Zifer, Manteca, CA (US); Gregory M. Jamison, Albuquerque, NM (US); Douglas A. Loy, Albuquerque, NM (US); Kamyar Rahimian, Albuquerque, NM (US); Timothy M. Long, Urbana, IL (US); David R. Wheeler, Albuquerque, NM (US); Chad L. Staiger, Albuquerque, NM (US)

(73) Assignee: Sandia Corporation, Livermore, CA (US)

( * ) Notice: Subject to any disclaimer, the term of this patent is extended or adjusted under 35 U.S.C. 154(b) by 586 days.

(21) Appl. No.: 11/394,294

(22) Filed: Mar. 29, 2006

Related U.S. Application Data (62) Division of application No. 10/866,475, filed on Jun. 10, 2004, now Pat. No. 7,022,861.

(51) Int. Cl.
*C07D 491/18* (2006.01)

(52) U.S. Cl. ..................................... 548/431
(58) Field of Classification Search ............... 516/102; 548/431
See application file for complete search history.

(56) References Cited

OTHER PUBLICATIONS

Long, T.M.; Simmons, B.A.; McElhanon, J.R. Kline, S.R.; J.R.; Wheeler, D.R.; Loy, D.A.; Rahimian, K.; Zifer, T.; and Jamison, G.M.;."Metathesis Depolymerization for Removable Surfactant Templates," *Langmuir*, 2005, v.21: pp. 9365-9373.

Jaeger, D.; Wang, Y.; Pennington, R.; "Pyrophosphate-Based Gemini Surfactants" *Langmuir*, 2002, v. 18: pp. 9259-9266.

*Primary Examiner*—Bernard Dentz
(74) *Attorney, Agent, or Firm*—Timothy P. Evans

(57) ABSTRACT

Two new surfactant molecules are reported which contain thermally labile Diels-Alder adducts connecting the polar and non-polar sections of each molecule. The two surfactants possess identical non-polar dodecyl tail segments but exhibit different polar headgroups. The surfactants become soluble in water when anionic salts are formed through the deprotonation of the surfactant headgroups by the addition of potassium hydroxide. When either surfactant is exposed to temperature above about 60° C., the retro Diels-Alder reaction occurs, yielding hydrophilic and hydrophobic fragments or the aqueous solutions of the surfactants subsequently exhibit loss of all surface-active behavior.

7 Claims, 10 Drawing Sheets

THERMALLY CLEAVABLE SURFACTANTS

CROSS REFERENCE TO RELATED APPLICATIONS

This application is a divisional application of prior U.S. patent application Ser. No. 10/866,475 originally filed Jun. 10, 2004 now U.S. Pat. No. 7,022,861 entitled "THERMALLY CLEAVABLE SURFACTANTS", which is herein incorporated by reference in its entirety.

STATEMENT OF GOVERNMENT INTEREST

The invention described below was made with Government support under government contract no. DE-AC04-94AL85000 awarded by the U.S. Department of Energy to Sandia Corporation. The Government has certain rights in the invention, including a paid-up license and the right, in limited circumstances, to require the owner of any patent issuing in this invention to license others on reasonable terms.

BACKGROUND

Over the past decade, the development of cleavable surfactants has been a growing field in surfactant science. As the name implies, cleavable surfactants are molecules that undergo a chemical or physical change of the parent molecular structure resulting in a change and/or loss of surface-active behavior. Hence, the production of commercially available cleavable surfactants would find utility in industrial practices where foaming or persistent surface-active properties must be diminished after their initial use, in "green" chemistry where biodegradability is of primary concern, and in biomedical drug delivery where surfactants could be removed through biological mechanisms.

Additionally, surfactant removal becomes increasingly significant in the synthesis of extended mesoporous and nanosized structures such as semiconductor nanocrystals, ceramics, polymers, and polymer-ceramic composites. The current techniques of surfactant removal are typically a combination of centrifugation, calcination, and solvent washing steps that can adversely affect and/or completely destroy the desired extended architecture and functionality of the synthesized material. Incorporation of a cleavable linkage into surfactant molecules could solve this problem by allowing the removal of the surfactant templates through the thermally keyed formation of small, easily removed fragments.

Several examples of cleavable surfactants have been previously reported based on functional groups that are susceptible to alkaline or acid hydrolysis. The surfactants operate at set pH ranges and are removed from the system by adding an appropriate amount of acid or base. Acid-labile surfactants include cationic surfactants with cyclic acetals such as cationic surfactants derived from bromopropionaldehyde, alkylglucosides, ortho esters, and both cyclic and noncyclic ketals (see for instance Wang, G.-W., et al., *Am. Oil Chemists Soc.* 1995, 72, p83; Rybinski, W.-V., *Curr. Opin. Colloid Interface Sci.* 1996, 1, p572; Eliason, R., et al., *J. Am. Chem. Soc.* 1978, 100, p7037; Jaeger, D. A., et al., *J. Org. Chem.* 1993, 58, p2619; and Ono, D., et al., *J. Org. Chem.* 1990, 55, p. 4461). Alkaline-labile surfactants include surfactants that contain cleavable ester moieties such as choline esters, esters of quaternized amidoamines and ethanolamines, as well as esters derived from naturally occurring sugars (i.e., glucose, sucrose, sorbitol) combined with fatty acids (see for instances Ahlstrom, B., et al., *Antimicrob. Agents Chemother.* 1995, 39, p50; Lagerman, R., et al., *J. Am. Oil Chemists Soc.* 1994, 71, p97; Swartley, D. M., et al., U.S. Pat. No. 5,399,272; and Ducret, A., et al., *J. Am. Oil Chemists Soc.* 1996, 73, p109). However, hydrolysable surfactants are disadvantaged and their utility limited due to the requisite addition of acid or base to degrade the surfactant, or in those applications where a neutral pH is required.

Other examples of cleavable surfactants wherein labile elements that have been incorporated into the surfactant molecule include UV sensitive components, such as alkylarylketone sulfonates and diazosulfonates which undergo surfactant cleavage upon irradiation (see Epstein, W. W., et al., *Anal. Biochem.* 1982, 119, p304; and Nuyken, O., et al., *J. Photochem. Photobiol. A Chem,* 1995, 85, p291), and some examples of amine oxide surfactants which decompose at temperatures above 100° C. (see Hayashi, Y., et al., *J. Am. Oil Chemists Soc.* 1985, 62, p555).

To overcome these shortcomings, we describe here the synthesis and characterization of two new surfactant compositions which incorporate a thermally cleavable Diels-Alder adduct as the chemical weak link within the surfactant molecular structure. In particular, we have utilized the reversible Diels-Alder reaction between functionalized furans and maleimides as the basis for a thermally cleavable material. We have previously reported the integration of furan-maleimide Diels-Alder adducts into molecules to produce thermally responsive encapsulating polymers, foams, and adhesives as well as dendrons and dendrimers which reversibly self-assemble (see U.S. Pat. Nos. 6,271,335; 6,337,384; and 6,403,753 and McElhanon, J. R., et al., *J. Appl. Pol. Sci.* 2002, 85, p. 1496; Aubert, J. H., *Journal of Adhesion* 2003, 79, pp. 609-616; and Aubert, J. H, U.S. Published Application No. 20030116272; McElhanon, J. R., et al., *Org. Lett.* 2001, 3(17), p. 2681). Also, similar thermally reversible Diels-Alder adducts have been reported incorporated into other responsive polymers (see Chen, X., et al., *Macromolecules* 2003, 36, p1802-1807; and Chen, X., et al., *Science* 2002, 295, p1698-1702).

SUMMARY

Figure 1A:
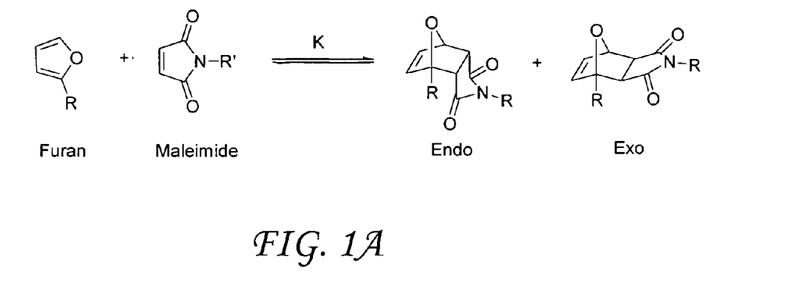
FIG. 1A illustrates the generalized scheme used to provide the Diels-Alder adduct from furan and maleimide.

We have utilized, therefore, the reversible Diels-Alder reaction between appropriately functionalized furans and maleimides as the basis for the two embodiments described below. The generalized process of adduct formation is shown in FIG. 1A and typically occurs at moderate temperatures, i.e., from about room temperature to about 60° C., whereas dissociation occurs at moderately elevated temperatures above about 60° C. Surfactant molecules which contain cleavable furan-maleimide Diels-Alder adducts are, therefore, attractive candidates as surface active materials for processes that require surfactant "deactivation" or removal using a non-invasive thermal trigger.

Accordingly, a method is herein disclosed for a thermally-cleavable surfactant which is prepared through the reversible Diels-Alder reaction between appropriately functionalized furans and a maleimide wherein the resultant molecule has the property that subsequent heating to a temperature greater than about 60° C. will cleave the molecule. It is therefore an object of this invention to provide a description of a method for preparing embodiments of thermally labile surfactants.

It is also an object of this disclosure to provide a description of two new surfactant molecules, and Gemini surfactant molecules.

It is yet another object of this disclosure to provide a description of a surfactant molecule that may be thermally cleaved through a retro Diels-Alder reaction.

Other embodiments of the invention, of course, will become apparent to those of skill in this art upon reading the description of the invention as it is taught and claimed in detail below and as illustrated in the appended drawings, briefly described as follows.

DETAILED DESCRIPTION AND BEST MODE

The present embodiment describes the preparation of a class of surfactant molecules which incorporate a short, thermally degradable "linker" species joining the head and tail groups of the surfactant molecule. In particular, surfactants of the present embodiment comprise simple ringed adduct species constructed by the well-known Diels-Alder reaction between appropriately functionalized furans and maleimides as the basis for these embodiments (FIG. 1A). As mentioned, the process of adduct formation typically occurs at moderate temperatures (i.e., room temperature up to about 60° C.), whereas dissociation occurs at elevated temperatures (>60° C.). Surfactant molecules that contain the furan-maleimide DA adducts are, therefore, attractive candidates as surface active materials for processes that require surfactant "deactivation" or removal using a non-invasive thermal trigger.

Figure 1B:
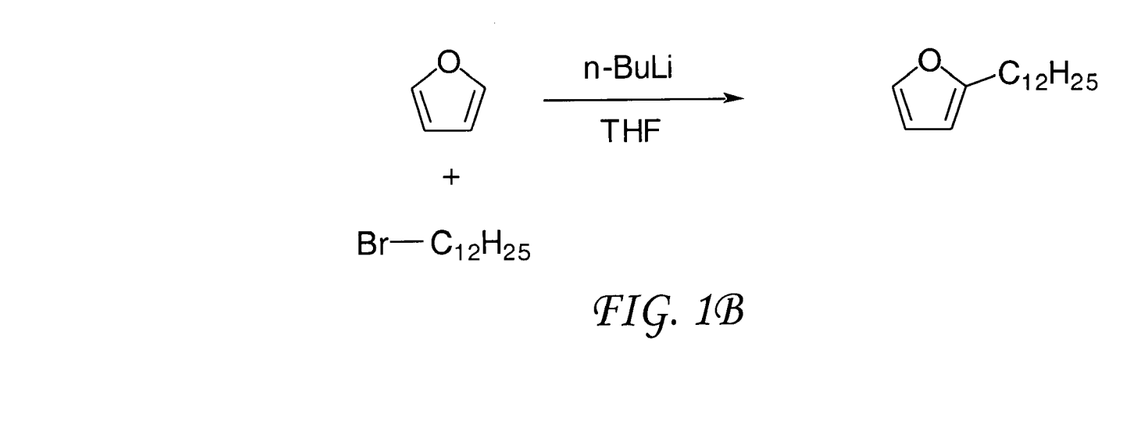
FIG. 1B shows the step of providing the alkylfuran precursor used in the present embodiments.
Figure 1C:
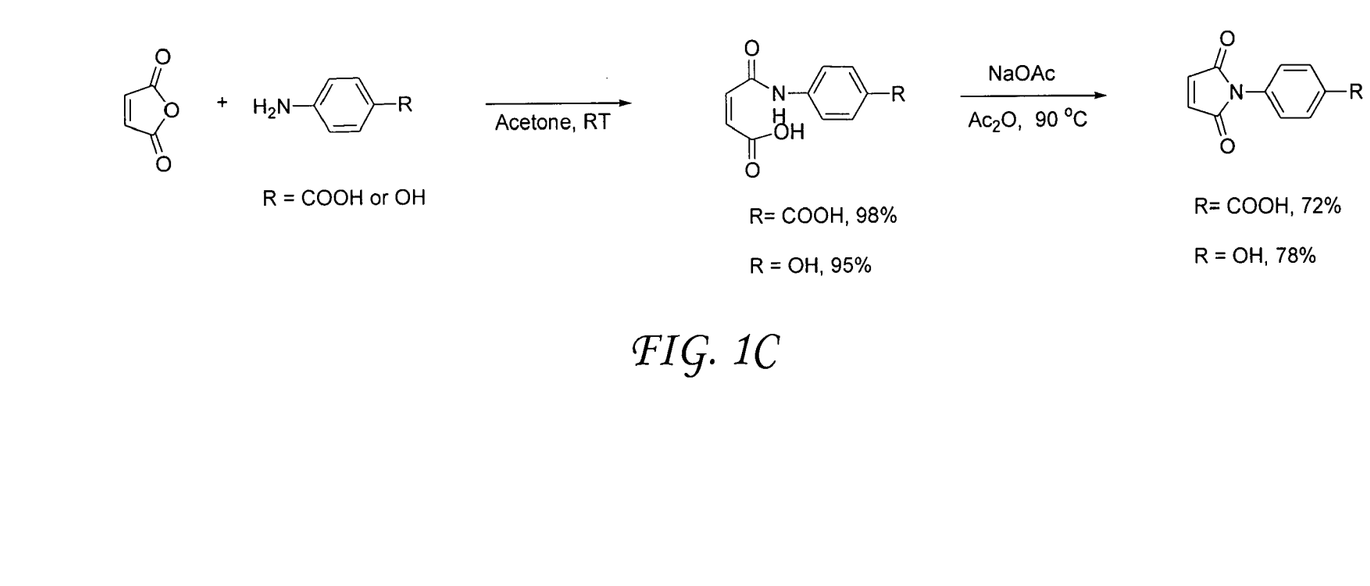
FIG. 1C shows the step of providing the functionalized maleimide precursor used in the present embodiment.

One of the present embodiments contemplates the use of an alkylfuran as the diene molecule and a maleimide incorporating a phenyl group as the dienophile molecule to produce the desired DA adduct molecule. In this way the alkylfuran carries with it the non-polar (hydrophobic) "tail" group for the nascent surfactant molecule while the maleimide carries the polar (hydrophilic) "head" group of the surfactant molecule as these two molecules are combined by the DA process. The alkylfuran is prepared as generally described by Piancatelli, et al., (*Tetrahedron*, v. 36, pp. 661-663, herein incorporated by reference) by a reaction between furan and an alkyl bromide molecule in a solution of n-butyl lithium and THF (shown in FIG. 1B). The functional maleimide is prepared as described by Park, et al., (*Poly. Sci. Part A: Poly. Chem.*, v. 30 (1992) pp. 723-729, herein incorporated by reference) by a condensation reaction to provide either a phenolated or a carboxylated maleimide. In the first case, 3- or 4-aminophenol is added to a solution of maleic anhydride in DMF followed by adding a solution of phosphorous pentoxide and sulfuric acid in DMF, (shown in FIG. 1C). In the second case, 3- or 4-aminobenzoic acid is first added to a solution of maleic anhydride and acetone to produce a precipitate of 3- or 4-carboxyphenyl maleamic acid which is purified by re-crystallization from a DMF/ethanol solution. This precipitate is then combined with acetic anhydride and sodium acetate and heated to 85° C.

The present embodiment, however, should not be construed as limiting the scope of the invention to any particular functional substituent. Neither should the embodiments be construed as restricted to attaching a tail group to furan and a headgroup to the maleimide molecules, since the opposite configuration is also possible. Surfactants contemplated as falling within the scope and meaning of the present invention, therefore, may use any of the head and tail groups known to the surfactant science arts that can be incorporated into the precursor molecules forming the basis for the DA cycloaddition reaction. In particular, tail groups comprising long alkyl chains, with or without branching, having the general formula $C_nH_2$, where n varies from 6 to about 24 and preferably from 6 to about 18, are considered as within the scope of the present disclosure as are any of the headgroups selected from the list of anionic groups, such as for instance, carboxylic acid salts, amine salts, sulfonic acid salts, sulfosuccinate esters, sulfuric acid ester salts, sulfated polyethylenated alcohols, sulfated triglyceride oils, and phosphoric and polyphosphoric acid esters; cationic groups, such as quaternary ammonium salts, amine salts, and amine oxides; and nonionic groups such as polyoxyethylenated alkyl phenols, alcohol ethoxylates, glycols, mercaptans, esters, alkanolamine, tertiary acetylenic glycols, pyrrolidones, alkylglycosides, and zwitterionic groups.

Moreover, the present invention also contemplates the class of surfactants known as "Gemini" surfactants. This class of molecules is important because they will provide the same surface-active behavior as "ordinary" surfactant molecules but at far lower concentrations. The Gemini molecules of the present invention contemplated attaching alkyl chains to both ends of the DA adduct, in this case a bismaleimide, through intermediate substituents attached to each end of the adduct. Moreover, any of the foregoing listed species may be used with the maleimide molecule to provide the surfactant headgroup for this class of surfactants.

EXAMPLES

Figure 1D:
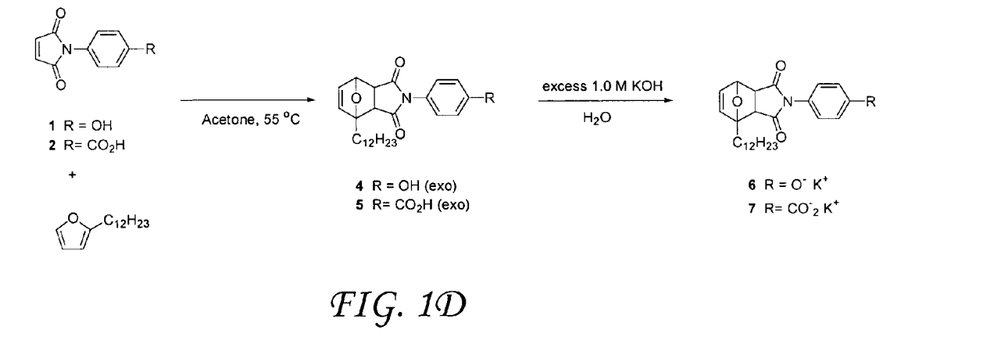
FIG. 1D shows the preparation of the surfactants of the present embodiment.

Reagent grade acetone, diethyl ether, chloroform, petroleum ether, and ethyl acetate were obtained from Aldrich Chemical Company, Inc and used as received. Reagent grade chemicals (1.0 N potassium hydroxide aqueous solution standard, triethylamine.) were obtained from Aldrich Chemical Company, Inc., and 30% KOD in $D_2O$ was obtained from Acros Organics, a division of Fisher Scientific. N-(4-hydroxyphenyl)maleimide (molecule 1), N-(4-carboxyphenyl)maleimide (molecule 2), and 2-N-dodecylfuran (molecule 3) were prepared according to the literature. Flash chromatography was performed by the method of Still et al., (Still, W. C.; Kahn, M.; Mitra, A. *J. Org. Chem.* 1978, 43, pp 2923-2925, herein incorporated by reference) using silica gel (200-400 mesh, 60 Å). Thin layer chromatography ("TLC") was performed on pre-coated TLC plates (silica gel, 250 μm Aldrich). All other reagents were purchased from commercial suppliers and used as received. Doubly filtered deionized water having a resistance of 18.2 Mohm was used for all experiments unless otherwise noted. The surfactant molecules of the present embodiments, therefore, were prepared as described below. The generalized reaction steps by which this was accomplished are shown in FIG. 1D.

Synthesis of Diels-Alder Surfactant—Phenolate Headgroup

One embodiment of the precursor surfactant molecule is prepared by providing a solution containing 3.15 g (16.6 mmol) of N-(4-hydroxyphenyl)maleimide (molecule 1) in 40 mL of acetone which is itself mixed with 5.62 g (23.8 mmol) of 2-n-dodecylfuran (molecule 3). This solution heated to 55° C. while stirred and allowed to react until TLC ($SiO_2$, 1:1 petroleum ether-ethyl acetate) showed consumption of the starting material. The reaction was then concentrated to dryness and the residue purified by flash chromatography on 60 Å silica gel in a 1:9 mixture of ethyl acetate and petroleum ether acting as a carrier solvent. This procedure provided 6.80 g (96% yield) of a colorless solid precursor material subsequently characterized using $^1H/^{13}C$ NMR and combustion analysis for confirmation of primary structure. The prepared isomer was identified as exo-4-dodecyl-7-oxabicyclo[2.2.1]hept-5-ene-2,3-dicarboxy-N-(4-hydroxyphenyl)imide and is designated, hereinafter, as molecule 4.

NMR spectra were measured at 500 MHz $^1H$ and at 125 MHz $^{13}C$, in $CDCl_3$, in DMSO-$d_6$, and in $D_2O$. Spectral results are as follows:

$^1H$ NMR (500 MHz, $CDCl_3$) δ 7.07 (d, J=9.0 Hz, 2H), 6.80 (d, J=8.5 Hz, 2H), 6.52 (dd, J=5.0, 2.0 Hz, 1H), 6.41, (d, J=6 Hz, 1H), 5.32 (s (br), 1H), 5.29 (d, J=1.5 Hz, 1H), 3.07 (d, J=6.5 Hz, 1H), 2.87 (d, J=6.5 Hz, 1H), 2.13-1.95 (m, 2H), 1.66-1.43 (m, 2H), 1.40-1.19 (m, 18H), 0.86 (t, J=7.5 Hz, 3H).

$^{13}C$ NMR (125 MHz, $CDCl_3$) δ 176.20, 174.72, 156.24, 139.12, 136.91, 127.92, 123.87, 116.14, 92.30, 80.82, 50.45, 49.00, 31.88, 29.91, 29.71, 29.63, 29.60, 29.52, 29.48, 29.31, 25.32, 22.65, 14.08.

Elemental analyses were performed by Gailbraith Laboratories of Knoxyille, Tenn. Analytically calculated for $C_{26}H_{35}NO_4$: C, 73.38; H, 8.29; N, 3.29. Found: C, 73.13; H, 8.49; N, 3.26.

Synthesis of Diels-Alder Surfactant—Carboxylate Headgroup

A second embodiment of the precursor surfactant molecule of the present invention is prepared by providing a solution in an essentially identical process as was used to prepare molecule 4. In the present embodiment, 3.68 g (16.9 mmol) of n-(4-carboxyphenyl)maleimide (molecule 2) was added to a solution of 5.72 g (24.2 mmol) of 2-n-dodecylfuran (molecule 3) and 30 mL of acetone and heated to 55° C. The solution was again stirred and allowed to react at 55° C. until TLC ($SiO_2$, 1:1 acetone-petroleum ether) indicated the starting materials had been consumed. The reaction was then concentrated to dryness, the residue purified by flash chromatography on 60 Å silica gel in a 1:4 mixture of acetone and chloroform acting as a carrier solvent and subsequently recrystallized in a mixture of chloroform and petroleum ether to yield 5.37 g (70% yield) of a second colorless solid precursor material again characterized using $^1H/^{13}C$ NMR and combustion analysis for confirmation of primary structure. The prepared isomer was identified as exo-4-dodecyl-7-oxabicyclo[2.2.1]hept-5-ene-2,3-dicarboxy-N-(4-carboxyphenyl)imide and is designated, hereinafter, as molecule 5.

As before, NMR spectra were measured at 500 MHz $^1H$ and at 125 MHz $^{13}C$, in $CDCl_3$, in DMSO-$d_6$, and in $D_2O$. NMR spectral results are as follows.

$^1H$ NMR (500 MHz, $CDCl_3$) δ 8.19 (d, J=8.5 Hz, 2H), 7.44 (d, J=9.0 Hz, 2H), 6.55 (dd, J=5.5, 1.5 Hz, 1H), 6.43 (d, J=6.0 Hz, 1H), 5.32 (d, J=1.5 Hz, 1H), 3.12 (d, J=6.5 Hz, 1H), 2.92 (d, J=6.5 Hz, 1H), 2.14-1.96 (m, 2H), 1.66-1.44 (m, 2H), 1.41-1.26 (m, 18H), 0.86 (t, J=7.0 Hz, 3H).

$^{13}C$ NMR (125 MHz, $CDCl_3$) δ 174.88, 173.48, 170.66, 139.24, 137.02, 136.47, 131.00, 129.08, 126.39, 92.48, 81.02, 50.59, 49.17, 31.90, 29.93, 29.72, 29.65, 29.62, 29.53, 29.48, 29.33, 25.34, 22.67, 14.10.

Elemental analyses were performed by Gailbraith Laboratories of Knoxyille, Tenn. Analytically calculated for $C_{27}H_{35}NO_5$: C, 71.50; H, 7.78; N, 3.09. Found: C, 71.60; H, 7.88; N, 3.06.

Preparation of Aqueous Surfactant Solutions

Aqueous solutions were prepared by dissolving carefully weighed amounts into is deionized water. All samples were contained in 20 mL glass scintillation vials and capped with Teflon sealed screw caps. The native precursor surfactant molecules 4 and 5 were found to have limited solubility in water. In order to enhance their solubility, the potassium salts of surfactants precursors 4 and 5 were prepared in situ through deprotonation of molecules 4 and 5 with excess amounts of potassium hydroxide (KOH) until completely clear and isotropic surfactant solutions were obtained. The amount of excess potassium hydroxide required to completely solubilize the surfactant was found to be dependent on the initial surfactant headgroup present. We found that a final minimum required molar ratios of 10:1 KOH:surfactant was necessary to solubilize precursor molecule 4 to produce phenolic surfactant solution 6 (hereinafter referred to as "phenolate salt 6" "phenolate surfactant 6", "surfactant 6", or simply as "molecule 6") and 1.7:1 KOH:surfactant to solubilize molecule 5 to produce carboxylic surfactant 7 (hereinafter referred to as "carboxylate salt 7", "surfactant 7", or simply as "molecule 7").

Surfactant Thermal Reversibility/Degradation

The onset of the thermally reversible reactions of molecules 4 and 5 in DMSO-$d_6$ solution were evaluated by $^1H$ NMR. Both molecules 4 and 5 were thermally stable up to about 50° C. at which point each molecule began to undergo the retro Diels-Alder reaction. Significant reversibility back to starting materials occurred at 60° C. for molecules 4 (7% dissociation) and 5 (13% dissociation) as evidenced by the appearance of characteristic resonances for molecules 1, 2, and 3 in the NMR spectra.

For example, the singlets appearing at 7.07 ppm for molecule 1 and 7.17 ppm for molecule 2 corresponding to the two equivalent alkene protons in each were diagnostic in evaluating the onset of the retro-Diels-Alder reaction for molecules 4 and 5, respectively. Solid state stability of molecules 4 and 5 at elevated temperatures was also evaluated. Solid samples were incrementally heated, cooled to room temperature, and evaluated by NMR. Molecule 4 was stable with the Diels-Alder adduct intact up to about 100° C. Upon heating to 105° C. the solid melted and $^1$H NMR revealed >95% dissociation to starting molecules 1 and 3.

Room temperature stability of surfactants 6 and 7 in water solution and retro Diels-Alder reactions at elevated temperatures were also investigated. $^1$H NMR samples of surfactants 6 and 7 were prepared through treatment of molecules 4 and 5 with appropriate amounts KOD in $D_2O$. Phenolate surfactant 6 exhibited stability up to 55° C. at which point some small amount of degradation occurred, not due to the retro Diels-Alder reaction, as evidenced by the appearance of anomalous peaks in the $^1$H NMR spectrum. Heating to 65° C. promoted surfactant 6 to undergo the retro Diels-Alder reaction with substantial reversibility occurring at 75° C., resulting in formation of molecule 3 and the potassium salt of molecule 4. Prolonged heating (3 hours) at 95° C. converted the potassium salt of molecule 4 to the corresponding ring opened maleamic acid salt due to the excess KOD concentration. Surfactant 7 exhibited a similar trend with stability up to 50° C. at which point the retro Diels-Alder reaction was activated with substantial reversibility occurring at 60° C. Alkylfuran molecule 3 was observed in addition to the potassium salt of molecule 2 which converted to the ring opened maleamic acid of molecule 2 upon heating at 95° C. in the presence of excess KOD for three hours.

Characterization of Surface Active Properties

The surfactants are characterized by determining the extent to which it exhibits surface-active properties. Two traditional methods are relied upon to achieve this: determining the extent to which the surfactant can solubilize a water-insoluble dye and its surface tension properties. In particular, the solubilization of a water-insoluble dye has been extensively used since the 1960's to indicate the presence of micelles. This technique is used herein to confirm the presence of micellar aggregates in the present surfactant solution and to determine the critical micelle concentration ("cmc"), above which these aggregates form.

Dye Solubilization

Small quantities of reagent grade Orange OT and Sudan III dyes were obtained from Aldrich Chemical Company, Inc. and used to investigate the enhanced solubility of a water-insoluble dye in the presence of micelles. Excess amounts (0.02 g per 10 mL of aqueous sample) of both Orange OT and Sudan III were added to separate concentration series of aqueous surfactant sample solutions and ultrasonically agitated for 30 minutes in a water bath using a sonication source operated at room-ambient conditions. After agitation, the sample solutions were removed from the water bath and allowed to settle for 2 hours, again at room-ambient conditions. Syringes were then filled with the samples and the samples subsequently filtered using 0.2 μm Whatman® PVDF syringe filters into 3.5 mL 1 cm path length quartz cuvettes obtained from Stama Cells, Inc., Atascadero, Calif. The amount of dye solubilized in each sample was measured by monitoring the absorbance profiles of each with a Shimadzu 2401-PC UV-Vis Dual Beam Spectrophotometer (Shimadzu Scientific Instruments, Columbia Md.) operating at ambient conditions with air serving as the sample reference.

Figure 2:
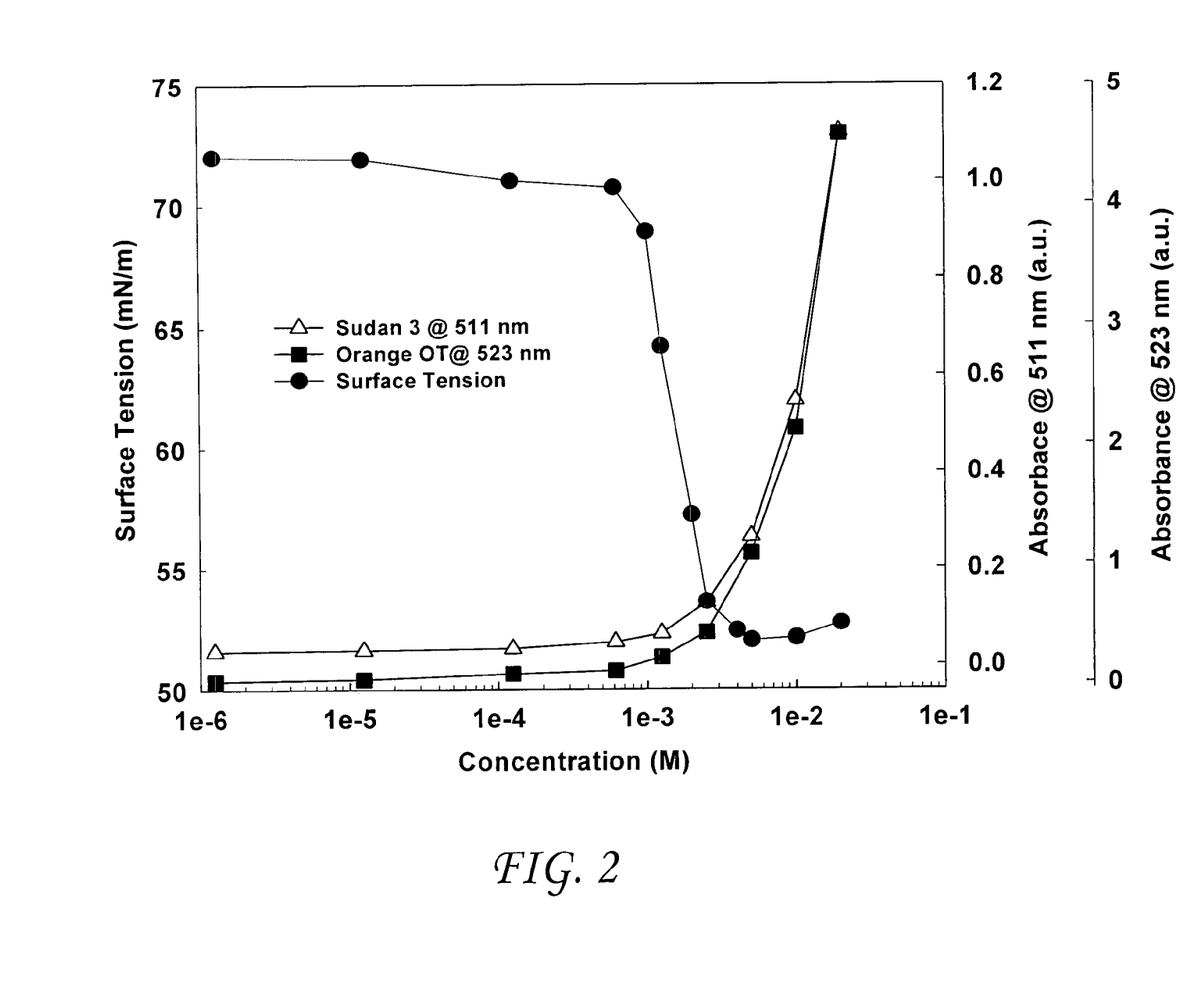
FIG. 2 shows a semi-log plot of critical micelle concentration determination of the phenolate surfactant 6 as determined by dynamic surface tension (operated at equilibrium mode) and dye solubilization measurements as a function of concentration at 26° C.
Figure 3:
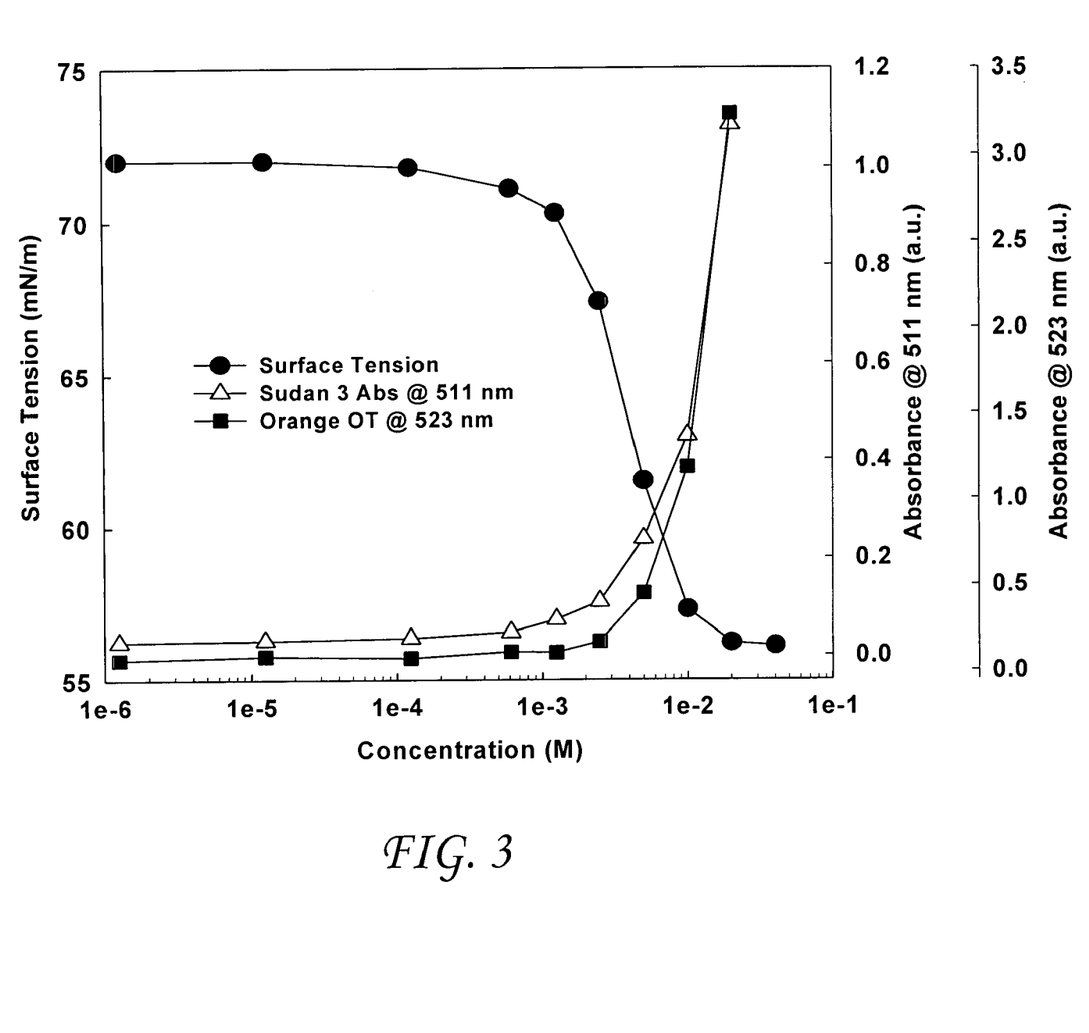
FIG. 3 shows a semi-log plot of critical micelle concentration determination of the phenolate surfactant 7 as determined by dynamic surface tension (operated at equilibrium mode) and dye solubilization measurements as a function of concentration at 26° C.

FIGS. 2 and 3 show the plots of the Orange OT and Sudan 3 dye absorbance values as a function of concentration for surfactants 6 and 7, respectively. The increase in absorbance of both dyes was monitored using the maximum wavelength for each of the dyes. The obtained values of absorbance versus increasing dye concentration are seen to exhibit an initial constant region (Region 1), a short transition region after a specific level has been reached, and a following linearly increasing region (Region 2). The linear dependence of Region 2 indicates the presence of micelles and is attributed to the increase in the amount of dye that is solubilized in the micellar cores of the surfactants. Critical micellar concentration, therefore, is defined as the intersection of lines fit to the set of points in Regions 1 and 2 in each surfactant system. The amount of dye solubilized by the micelles can be expressed as $$S = b/(\epsilon L) \tag{1}$$

where S is the amount of dye solubilized, b is the slope of the line fitted to the linear region of the data in FIGS. 2 and 3, $\epsilon$ is the extinction coefficient of the dye (17,400 L/mol-cm for Orange OT and 28,766 L/mol-cm for Sudan 3), and L is the path length (1 cm in the present case). The values obtained for dye solubilization in each surfactant system are in general agreement with each other and are presented in TABLE 1 below. The solubilizing power of both surfactants appears relatively equal for each respective dye, as expected since each possesses identical non-polar segments and differ only in terms of the headgroup character.

TABLE 1

Physicochemical Properties of the Surfactants

| | cmc$^a$ (mmol) | cmc$^b$ (mmol) | cmc$^c$ (mmol) | Γ (mol/cm$^2$) | $a_{HG}$ (Å$^2$) | $\Delta G°_{mic}$ (kJ/mol) | $S_{Orange\ OT}$ | $S_{Sudan\ 3}$ |
|---|---|---|---|---|---|---|---|---|
| 6 | 2.8 | 0.6 | 0.7 | 6.59 × 10$^{-10}$ | 25.2 | −24.5 | 1.34 × 10$^{-2}$ | 1.92 × 10$^{-3}$ |
| 7 | 10.1 | 2.7 | 1.4 | 2.61 × 10$^{-10}$ | 63.6 | −21.3 | 1.02 × 10$^{-2}$ | 1.94 × 10$^{-3}$ |

$^a$As determined by surface tensiometry
$^b$As determined by Orange OT dye solubilization
$^c$As determined by Sudan 3 dye solubilization FIGS. 2 and 3 also show the response of dynamic surface tension values (operated in equilibrium mode) measured as a function of concentration for the anionic salts 6 and 7 in aqueous solution. The physicochemical properties of a surfactant change to a significant degree after reaching the cmc due to the presence of the micelles and a surfactant saturated air-water interface. The surface excess concentration, Γ, and the area per molecule at the interface, a, have been determined using the standard Gibbs equation for anionic surfactants with a swamping amount of electrolyte, which in this case is due to the excess KOH added to solubilize the surfactants, expressed as:

$$\Gamma = -\frac{1}{2.3RT}\left(\frac{d\gamma}{d\log C}\right)_T, \text{ and} \quad (2)$$

$$a = \frac{10^{18}}{N_A \Gamma} \quad (3)$$

where R is the gas constant; T is the temperature at which the measurements were made (in this case, 26° C.±0.2° C.); γ is the surface tension; C is the surfactant concentration; and $N_A$ is Avogadro's number.

A comprehensive listing of all the physicochemical properties calculated for these surfactants is shown above in TABLE 1. As seen in FIGS. 2 and 3, both embodiments of the surfactants exhibited the classical dependence of surface tension as a function of concentration. In particular, both exhibit a region at low concentrations having a generally constant surface tension that transition smoothly to an intermediate concentration range in which surface tension decreases linearly, that again smoothly transitions into a region having a roughly constant surface tension at higher concentration. The concentration at the inflection point of the curve is referred to as the cmc. Qualitatively, it is observed that the slope of the linear region for surfactant 6 is steeper than that for surfactant 7, indicating that the phenolic-based anionic surfactant assembles at the liquid-gas ("L/G") interface with tighter packing when compared to surfactant 7. This is observed quantitatively when comparing the calculated surface excess concentrations of each, which are $6.59\times10^{-10}$ mol/cm² for surfactant 6 and $2.61\times10^{-10}$ mol/cm² for surfactant 7. This result indicates that surfactant 7 has a lower saturation level of free surfactant present at the L/G interface and infers that surfactant 7 forms a less tightly packed surfactant layer. These differences are probably due to the increased electrostatic repulsions between the carboxylate headgroups (which results in an increased hydrophilicty as well) when compared to that of phenolate 6.

The cmc of each surfactant was calculated by utilizing a least-squares fit of the linear region of the surface tension data and determining the intersection of that line with the constant surface tension values obtained at higher concentrations. The cmc's calculated from the surface tension data of surfactants 6 and 7 are 2.8 mmol and 10.1 mmol, respectively. This difference in cmc is attributed to the increased electrostatic repulsions between the carboxylate headgroups when compared to the same effect between the phenolate headgroups. Overall, the cmc's determined through this method are higher than those obtained by the measurement of dye solubilization described above. This discrepancy is generally attributed to static (dye solubilization) vs. dynamic (surface tension) measurements of the microenvironment. From the perspective of surface tension values at concentrations greater than the cmc, surfactant 6 attains a lower surface tension and thus appears to be a more active surfactant at the L/G interface than surfactant 7. The corresponding areas per surfactant molecule at the L/G interface calculated also indicate that carboxylate salt 7 occupies a much larger area per surfactant molecule (63.6 Å²) than phenolate salt 6 (25.2 Å²).

Surfactants 6 and 7 form micelles at relatively low concentrations and the standard free energy of micellization, $\Delta G_m^\circ$, was therefore determined by using the equation:

$$\Delta G_m^o = RT\ln\frac{cmc}{w} \quad (4)$$

where w is the molar concentration of water at ambient conditions listed in TABLE 1. Both surfactants produce negative values for their respective free energy values and are energetically favorable processes, with surfactant 6 the more negative of the two (−24.5 kJ/mol compared to −21.3 kJ/mol).

Figure 4:
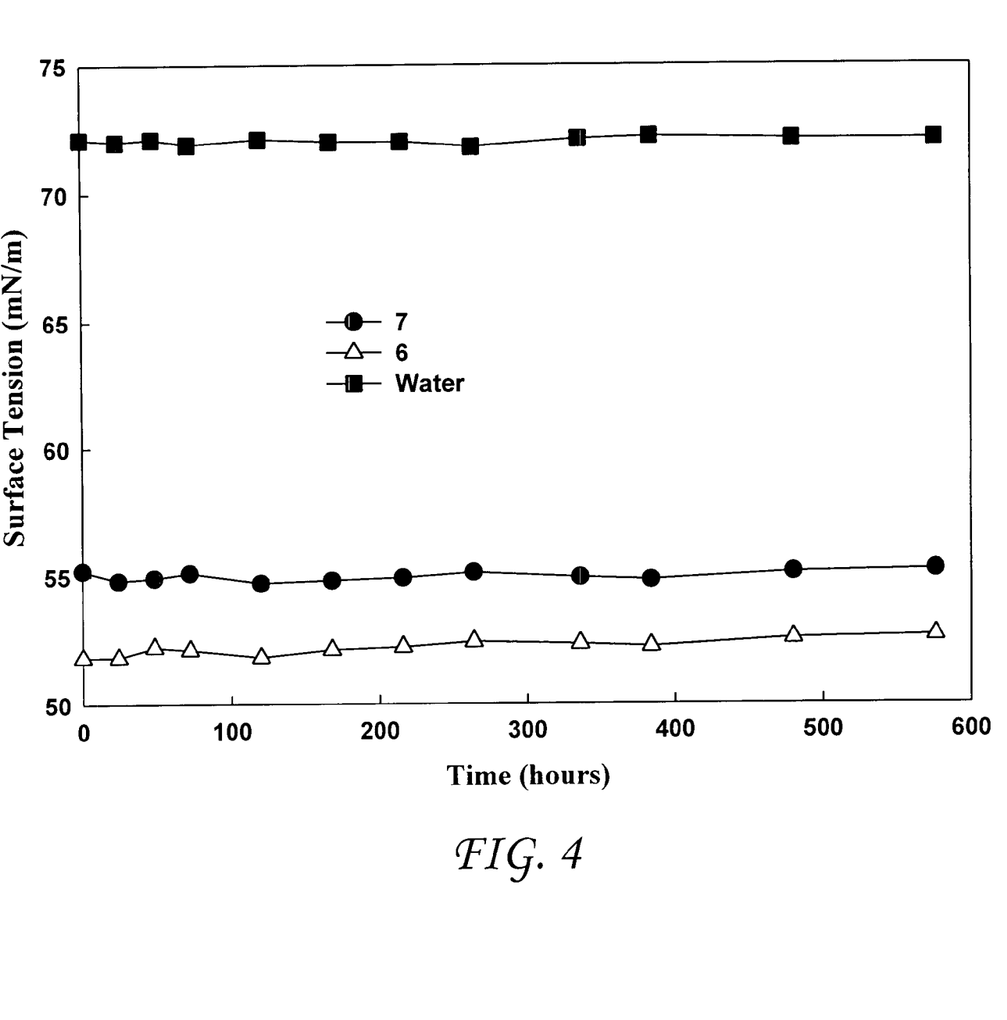
FIG. 4 shows the dynamic surface tension measurements (operated in equilibrium mode) as a function of time at 26° C. for anionic surfactants 6 and 7, with the surface tension of water measured as a point of reference. Surfactant concentration was held constant at 15 mM for both surfactants.

To determine the stability of these surfactants in solution, a room temperature aging study was conducted for each. The results, shown in FIG. 4, indicate that the surface tension values remain relatively constant for both surfactants over an extended time period (580 hrs) and do not suffer significant degradation. It should be noted, however, that an increase in solution turbidity did occur after 120 hours for surfactant 7 and 168 hours for surfactant 6. This turbidity did not appear to affect the surface tension measurements, but may indicate either a decrease in solubility or partial degradation of the surfactant under these conditions.

Dynamic Surface Tension/Response to Temperature

Surface tension measurements were conducted using a SensaDyne (Mesa, Ariz.) QC3000 dynamic surface tensiometer that utilizes the maximum bubble pressure method. The fundamental operating principles and theoretical considerations of this method are explained in detail elsewhere, and a brief summary only is given here. Two glass probes with different orifice diameters (0.5 and 4.0 mm) are submerged in an aqueous surfactant solution and nitrogen is bubbled through the samples. Dry nitrogen was used as the bubble source gas and was delivered to the instrument at 50 psi. The instrument was operated at the slowest recommended bubble rate (0.5 Hz) possible for this instrument to approximate equilibrium surface tension values for each sample. The differential pressure signal generated by bubble formation is related to the interfacial surface tension of the liquid and gas. Surface tension calibration was carried out by measuring the surface tension of deionized water and ethanol and compared to known literature values. Solution temperature was monitored with a calibrated thermistor (±0.1° C.) attached to the orifice probes. Instrumental calibration was conducted for every change in experimental conditions and after prolonged periods of instrumental quiescence. All experiments were conducted at 26.0° C.±0.2° C. unless otherwise noted. To determine the effect of temperature on surface tension as a measurement of surfactant degradation, the samples were heated at 95° C. for specified time intervals, allowed to cool to room temperature, and then analyzed. Data was recorded for all experiments via a computer interface using the SensaDyne QC3000 version 5.3 software.

Figure 5:
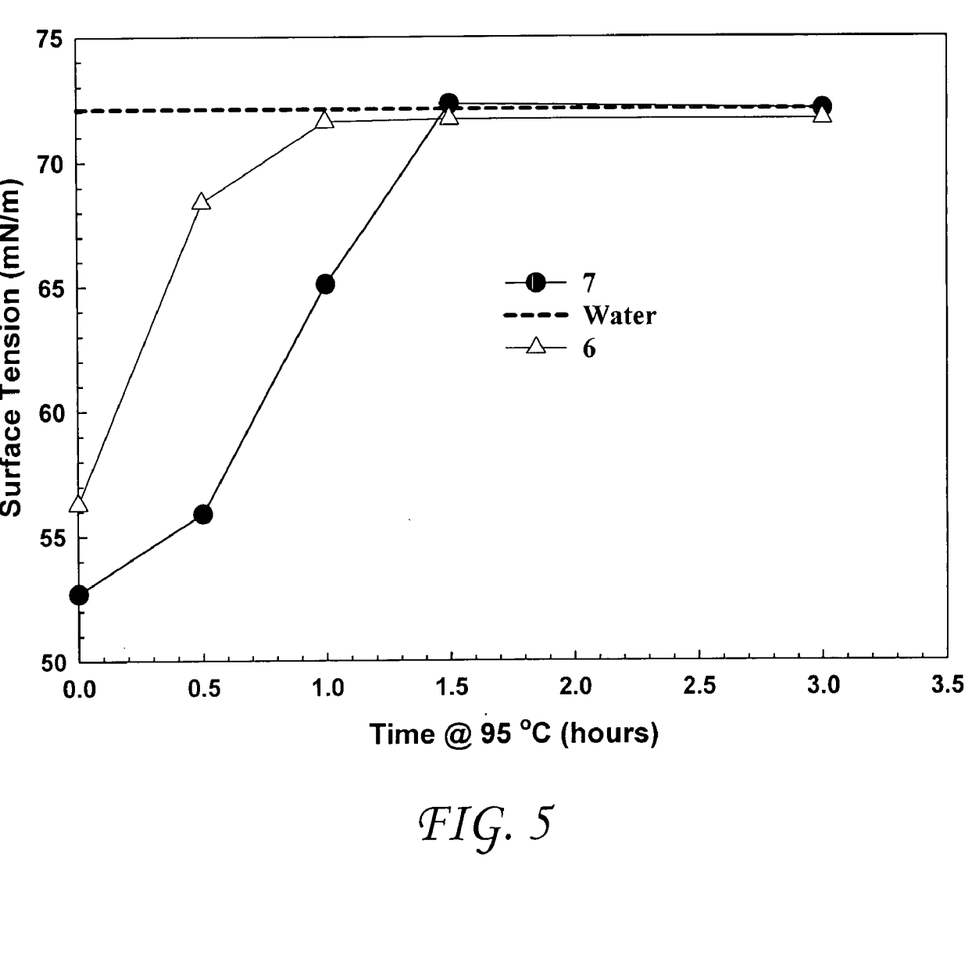
FIG. 5 shows the changes in dynamic surface tension (operated in equilibrium mode) as a function of time exposed to 95° C. for 20 mM aqueous solutions of anionic surfactants 6 and 7. Dotted line represents the surface tension value of water at 25° C. (72.1 mN/m).

The effect of elevated temperature (95° C.) on 20 mmol surfactant solutions of surfactants 6 or 7 and resulting change in surface tension due to the retro Diels-Alder reaction was determined. Visually, the solutions undergo a marked color change from clear and colorless to dark yellow and opaque with increased turbidity when exposed to elevated temperatures. Samples were also observed to phase separate when allowed to stand overnight. The response of the surface tension as a function of time at 95° C. is presented in FIG. 5. Both surfactants undergo a loss of surface tension after exposure to this temperature. The surface tension value for surfactant 7 reaches the value of water (72.1 mN/m) in approximately 1 hour and then stabilizes, whereas it takes 1.5 hour for surfactant 6 to reach the same plateau range. This difference is ascribed to the different cmc's for each surfactant, as you must reach a lower concentration for surfactant 6 before observing a substantial loss of surface tension when compared to surfactant 7 which has a higher cmc. In other words, for the same rate of dissociation it will require more time for the surface tension measurements of surfactant 6 to be affected by surfactant dissociation compared to surfactant 7. It should also be noted that the measurements of surface tension were taken after the samples had cooled, and indicate that this dissociation process is irreversible as there is no re-emergence of surface activity to lower initial values.

Synthesis of Diels-Alder "Gemini" Surfactants

Synthesis of a dimer, or "Gemini" DA surfactant, proceeds much the same as with the phenolate and carboxylate surfactants described above. The structure of the dimer can comprise two surfactant molecules attached to a bismaleimide or a bisfuran, where the surfactant molecules comprise a non-polar branched or unbranched alky group coupled to an ionic polar group, such as a quaternary ammonium group.

Figure 6A:
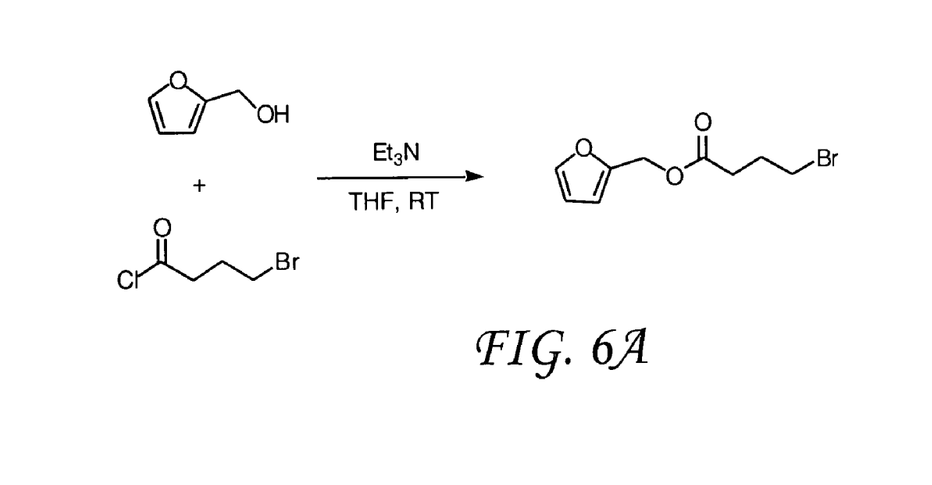
FIG. 6A illustrates the synthesis scheme for preparing the Gemini surfactants of the present embodiments.
Figure 6B:
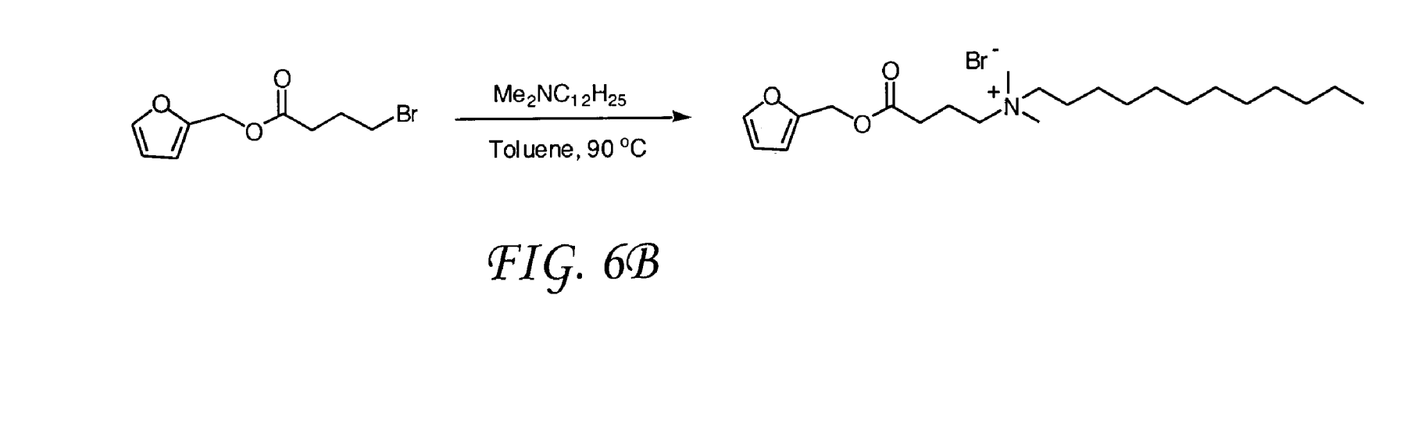
FIG. 6B illustrates the synthesis scheme for preparing the Gemini surfactants of the present embodiments.

In an embodiment comprising the bismaleimide, the Gemini surfactant is synthesized as follows. The diene precursor is prepared in a first step, shown in FIG. 6A, by mixing furfuryl alcohol to a solution of 4-bromobutyryl chloride in triethylamine and THF at room temperature. This first reaction step produces the functionalized furan molecule (molecule 1*) with a reactive bromine atom attached to the end of the functional group. In a second step, shown in FIG. 6B, the functionalized furan intermediate molecule 1* is modified by adding it to a solution of N,N dimethyl-dodecylamine and toluene and heated to 90° C. for 24 hours to produce an intermediate molecule, (molecule 2*). Intermediate molecule 2* is formed by attaching the alkyl amine, comprising part of the solution in step 2, at the site of the bromine atom of molecule 1* through a substitution reaction between the bromine atom and the amine group of the alkyl amine. The resulting bromine ion, however, remains as a counter ion to balance the charge of the newly formed ammonium group. Molecule 2*, itself a surfactant molecule, comprises the diene precursor used in the Diels-Alder reaction to provide the Gemini surfactant.

Figure 6C:
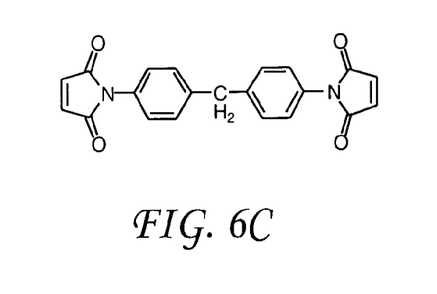
FIG. 6C illustrates the synthesis scheme for preparing the Gemini surfactants of the present embodiments.

The dienophile of this embodiment is shown in FIG. 6C. It comprises two phenyl maleimide groups joined at position 4 of each of the phenyl rings by a short alkyl group to form a bismaleimide. The particular molecule used was 1,1'-(Methylenedi-4,1-phenylene) bismaleimide. Other substituents are possible, of course, including all of the polar groups recited earlier.

Figure 6D:
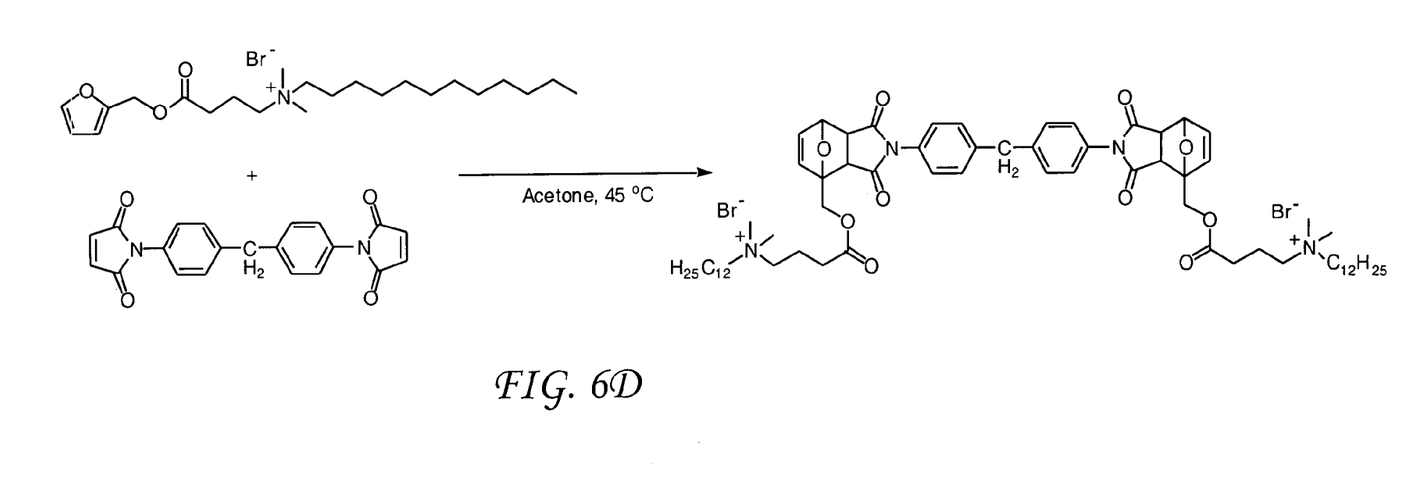
FIG. 6D illustrates the synthesis scheme for preparing the Gemini surfactants of the present embodiments.

The Gemini surfactant of this embodiment was formed in a third step shown in FIG. 6D by adding two equivalents of molecule 2* to a quantity of the 1,1'-(methylenedi-4,1-phenylene) bismaleimide and acetone. This solution was then heated to 45° C. for about 72 hours to produce Gemini surfactant molecule 3* shown as the reaction product of step 3 in FIG. 6D.

The Gemini molecules of the present invention, therefore, comprise alkyl chains attached to both ends of the DA adduct, in this case a bismaleimide, through intermediate substituents attached to each end of the adduct. Moreover, any of the foregoing listed species may be used with the maleimide molecule to provide the headgroup for this class of surfactants and any branched or un-branched alkyl amine of the general formula $C_nH_{2n}N(H_3C)_2$, where n may vary from at least about 8 to about 18, to provide the tailgroup. Furthermore, as herein noted earlier, we believe that the same result would be achieved by substituting a bisfuran for the bismaleimide as the central connecting group in the dimer and substituting an alkyl maleimide as the substituent containing a polar and non-polar group.

Figure 7:
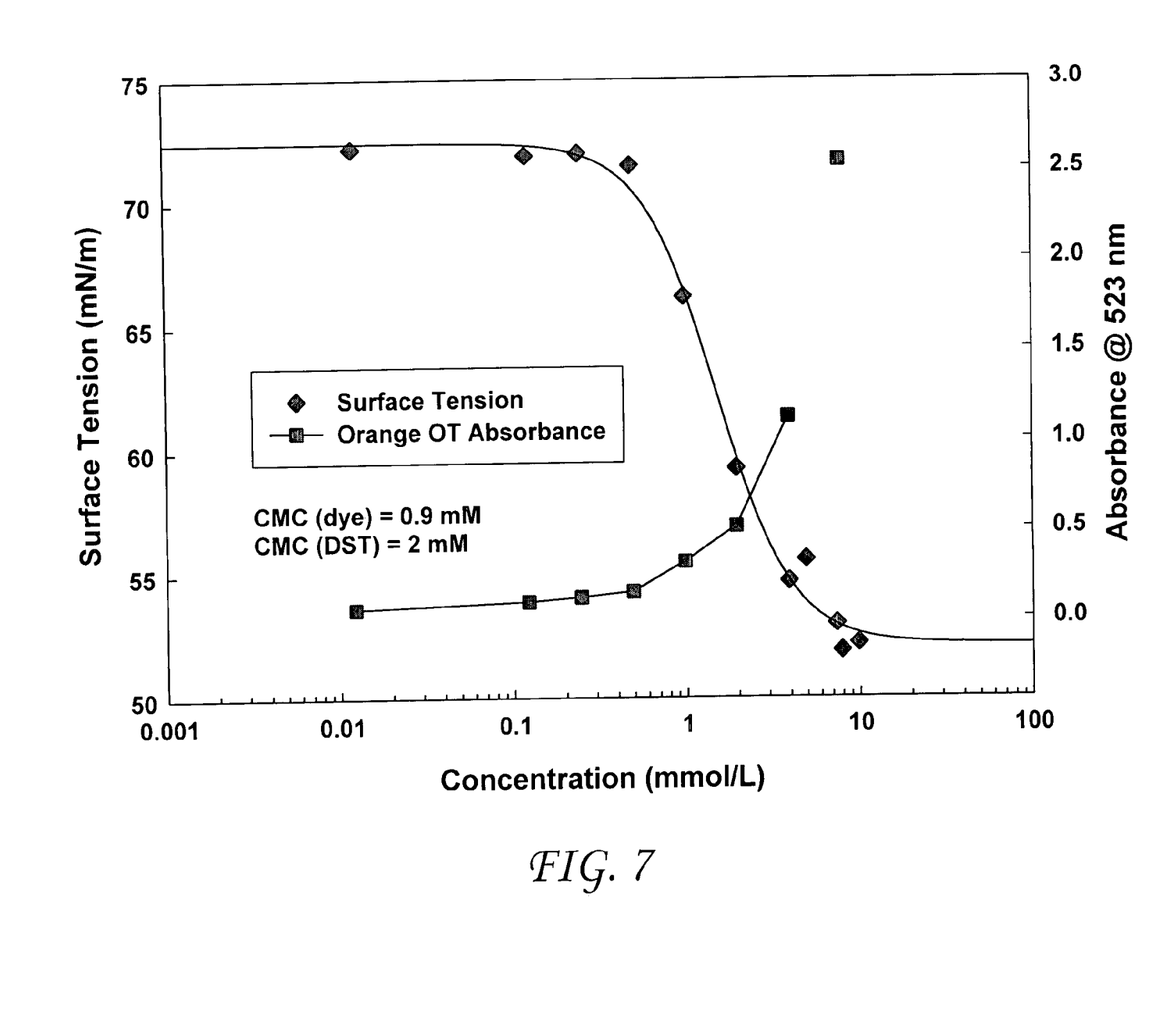
FIG. 7 shows a semi-log plot of critical micelle concentration determination of the Gemini surfactant of the present embodiment as determined by dynamic surface tension (operated at equilibrium mode) and dye solubilization measurements as a function of concentration at 26° C.
Figure 8:
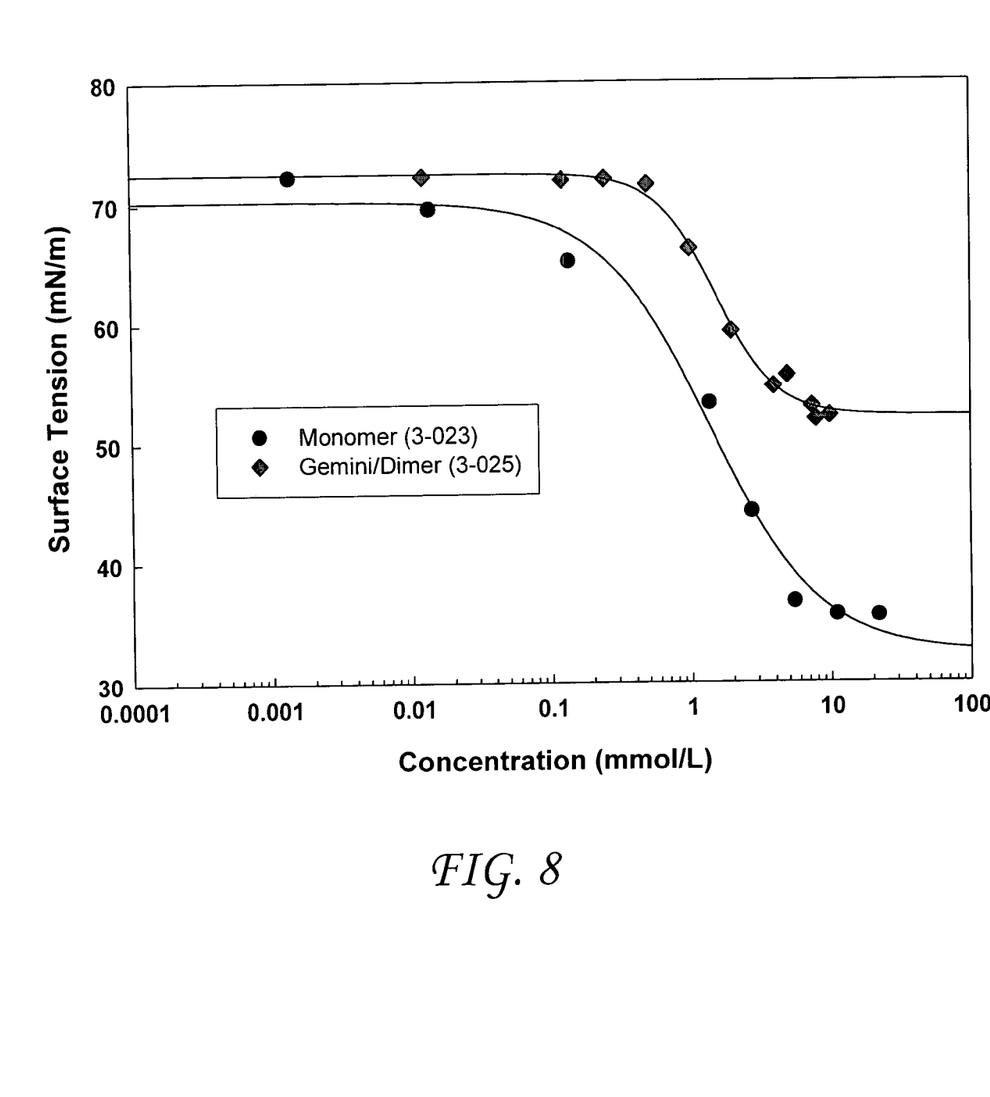
FIG. 8 shows a comparison of the measured surface tensions of surfactant 6 and the Gemini surfactant of the present embodiments.

Finally, as shown in FIGS. 7 and 8, the Gemini surfactants of these embodiments exhibit surface active behavior very similar to that exhibited by the monomeric phenolate and carboxylate surfactants described earlier.

We claim:

1. A thermally cleavable Gemini surfactant compound, comprising
   a Diels-Alder adduct of a bismaleimide molecule and
   a first functionalized furan molecule attached at a first end of the bismaleimide molecule and a second functionalized furan molecule attached at a second end of the bismaleimide molecule, the functionalized furan molecule having one or more polar and non-polar functional groups attached thereto.

2. The compound of claim 1, wherein the polar functional groups comprise one of an anionic polar group, a polar cationic group, or a nonionic polar group.

3. The compound of claim 2, wherein the anionic polar group is selected from the list consisting of carboxylic acid salts, amine salts, sulfonic acid salts, sulfosuccinate esters, sulfuric acid ester salts, sulfated polyethylenated alcohols, sulfated triglyceride oils, and phosphoric and polyphosphoric acid esters.

4. The compound of claim 2, wherein the cationic polar group is selected from the list consisting of quaternary ammonium salts, amine salts, and amine oxides.

5. The compound of claim 2, wherein the nonionic polar group is selected from the list consisting of polyoxyethylenated alkyl phenols, alcohol ethoxylates, glycols, mercaptans, esters, alkanolamine, tertiary acetylenic glycols, pyrrolidones, alkylglycosides, and zwitterionic groups.

6. The compound of claim 2, wherein the non-polar functional groups comprise an alkyl group.

7. The compound of claim 6, wherein the alkyl group is prepared by the addition of a reactive bromine atom distal to the furan molecules and the addition of branched or unbranched alkyl amines having the general formula $C_nH_{2n}N(H_3C)_2$ wherein n varies from 6 to about 18.

* * * * *